(12) United States Patent
Orszulak et al.

(10) Patent No.: US 9,439,717 B2
(45) Date of Patent: Sep. 13, 2016

(54) SURGICAL FORCEPS INCLUDING THERMAL SPREAD CONTROL

(71) Applicant: COVIDIEN LP, Mansfield, MA (US)

(72) Inventors: James H. Orszulak, Nederland, CO (US); J. Bruce Dunne, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 263 days.

(21) Appl. No.: 14/253,017

(22) Filed: Apr. 15, 2014

(65) Prior Publication Data

US 2015/0051598 A1 Feb. 19, 2015

Related U.S. Application Data

(60) Provisional application No. 61/865,467, filed on Aug. 13, 2013.

(51) Int. Cl.
*A61B 18/14* (2006.01)
*A61B 18/00* (2006.01)

(52) U.S. Cl.
CPC .... *A61B 18/1445* (2013.01); *A61B 2018/0016* (2013.01); *A61B 2018/00047* (2013.01); *A61B 2018/0063* (2013.01); *A61B 2018/00196* (2013.01); *A61B 2018/00601* (2013.01); *A61B 2018/00642* (2013.01); *A61B 2018/00702* (2013.01); *A61B 2018/00797* (2013.01); *A61B 2018/1455* (2013.01)

(58) Field of Classification Search
CPC ............... A61B 18/1445; A61B 2018/00047; A61B 2018/0016; A61B 2018/00196; A61B 2018/00601; A61B 2018/0063; A61B 2018/00642; A61B 2018/00702; A61B 2018/00797; A61B 2018/1455
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 08/926,869, field Sep. 10, 1997, James G. Chandler.

(Continued)

*Primary Examiner* — Daniel Fowler (57) ABSTRACT

A surgical instrument includes one or more electrically-conductive plates adapted to connect to a source of energy for supplying energy to tissue to treat tissue, a temperature sensing element, and a thermal spread control assembly coupled to the temperature sensing element. The thermal spread control assembly is configured to determine a flow rate of heat energy across the temperature sensing element and to control the energy applied to the electrically-conductive plate and/or control active cooling of the temperature sensing element in accordance with the determined flow rate of heat energy.

20 Claims, 5 Drawing Sheets

(56) References Cited

U.S. PATENT DOCUMENTS

| | | |
|---|---|---|
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,755,717 A | 5/1998 | Yates et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,656,177 B2 | 12/2003 | Truckai et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,169,146 B2 | 1/2007 | Truckai et al. |
| D538,932 S | 3/2007 | Malik |
| D541,418 S | 4/2007 | Schechter et al. |
| 7,204,832 B2 | 4/2007 | Altshuler et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| 7,238,184 B2 | 7/2007 | Megerman et al. |
| D564,662 S | 3/2008 | Moses et al. |
| 7,347,856 B2 | 3/2008 | Wittenberger et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,708,735 B2 | 5/2010 | Chapman et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,918,848 B2 | 4/2011 | Lau et al. |
| 7,931,649 B2 | 4/2011 | Couture et al. |
| D649,249 S | 11/2011 | Guerra |
| D649,643 S | 11/2011 | Allen, IV et al. |
| 8,128,624 B2 | 3/2012 | Couture et al. |
| D661,394 S | 6/2012 | Romero et al. |
| 8,197,472 B2 | 6/2012 | Lau et al. |
| 8,207,651 B2 | 6/2012 | Gilbert |
| 8,216,223 B2 | 7/2012 | Wham et al. |
| 8,388,647 B2 | 3/2013 | Nau, Jr. et al. |
| RE44,834 E | 4/2014 | Dumbauld et al. |
| 2006/0217709 A1 | 9/2006 | Couture et al. |
| 2008/0281316 A1* | 11/2008 | Carlton ............ A61B 18/1445 606/40 |
| 2010/0094271 A1 | 4/2010 | Ward et al. |
| 2013/0197503 A1* | 8/2013 | Orszulak ........... A61B 18/1206 606/33 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |

(56) References Cited

FOREIGN PATENT DOCUMENTS

| | | |
|---|---|---|
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 2006/021269 A1 | 3/2006 |
| WO | 2005110264 A3 | 4/2006 |
| WO | 2008/040483 A1 | 4/2008 |
| WO | 2011/018154 A1 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Schmaltz et al.
U.S. Appl. No. 09/591,328, filed Jun. 9, 2000, Ryan et al.
U.S. Appl. No. 12/336,970, filed Sep. 17, 2008, Sremcich et al.
U.S. Appl. No. 13/731,674, filed Dec. 31, 2012, Siebrecht.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'L Federation of Gynecology and Obstetrics (FIGO) World Congress 1999.
Barbara Levy, "Use of a New Vessel Ligation Device During Vaginal Hysterectomy" FIGO 2000, Washington, D.C.

(56) References Cited

OTHER PUBLICATIONS

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'L Federation of Gynecology and Obstetrics FIGO World Congress 2000, Washington, D.C.

McLellan et al. "Vessel Sealing for Hemostasis During Gynecologic Surgery" Sales/Product Literature 1999.

\* cited by examiner

SURGICAL FORCEPS INCLUDING THERMAL SPREAD CONTROL

CROSS REFERENCE TO RELATED APPLICATION

The present application claims the benefit of and priority to U.S. Provisional Application Ser. No. 61/865,467, filed on Aug. 13, 2013, the entire contents of which are incorporated herein by reference.

BACKGROUND

1. Technical Field

The present disclosure relates to surgical devices and, more particularly, to surgical forceps and end effector assemblies thereof for controlling thermal spread during energy-based tissue treatment and/or energy-based tissue cutting.

2. Background of Related Art

A surgical forceps is a plier-like device which relies on mechanical action between its jaws to grasp, clamp, and constrict tissue. Energy-based surgical forceps utilize both mechanical clamping action and energy to affect hemostasis by heating tissue to coagulate and/or cauterize tissue. Certain surgical procedures require more than simply cauterizing tissue and rely on the unique combination of clamping pressure, precise energy control and gap distance (i.e., distance between opposing jaw members when closed about tissue) to "seal" tissue. Typically, once tissue is sealed, the surgeon has to accurately sever the tissue along the newly formed tissue seal. Accordingly, many tissue sealing devices have been designed which incorporate a knife or blade member which effectively severs the tissue after forming a tissue seal. More recently, tissue sealing devices have incorporated energy-based cutting features for energy-based tissue division.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, a surgical instrument is provided. The surgical instrument includes one or more electrically-conductive plates adapted to connect to a source of energy for supplying energy to tissue to treat tissue, a temperature sensing element, and a thermal spread control assembly coupled to the temperature sensing element. The thermal spread control assembly is configured to determine a flow rate of heat energy across the temperature sensing element and to control the energy applied to the electrically-conductive plate and/or control active cooling of the temperature sensing element in accordance with the determined flow rate of heat energy.

In aspects, the temperature sensing element is incorporated into the electrically-conductive plate. Alternatively, the temperature sensing element may be disposed about an outer periphery of the electrically-conductive plate.

In aspects, a thermoelectric cooler is coupled to the temperature sensing element for actively cooling the temperature sensing element. The thermal spread control assembly may be configured to control power supplied to the thermoelectric cooler to vary an amount of cooling provided by the thermal spread control assembly. Further, a thermally-conductive, electrically insulative material may be disposed between the thermoelectric cooler and the temperature sensing element.

In aspects, the thermal spread control assembly is configured to measure a temperature at each of a first side and a second side of the temperature sensing element to determine a temperature differential therebetween. Further, the thermal spread control assembly may be configured to determine the flow rate of heat energy across the temperature sensing element in accordance with the temperature differential and a thermal conductivity of the temperature sensing element.

In aspects, the electrically-conductive plate and the temperature sensing element are disposed within an end effector assembly of the surgical instrument. The thermal spread control assembly may likewise be disposed within the end effector assembly, or may be remotely positioned relative to the end effector assembly.

In aspects, the thermal spread control assembly performs control in accordance with the determined flow rate of heat energy to maintain the flow rate of heat energy within a predetermined range. Alternatively, the thermal spread control assembly may be configured to perform control in accordance with the determined flow rate of heat energy to maintain the flow rate of heat energy below a predetermined threshold.

In accordance with the present disclosure, a method of treating tissue is provided including applying energy to tissue, determining a flow rate of heat energy across a temperature sensing element, and controlling the energy applied to tissue and/or controlling active cooling of tissue based upon the flow rate of heat energy.

In aspects, applying energy to tissue includes grasping tissue between first and second electrically-conductive plates and conducting energy therebetween. In such aspects, determining the flow rate of heat energy across the temperature sensing element may include determining the flow rate of heat energy across the first and/or second electrically-conductive plates. Alternatively, determining the flow rate of heat energy across the temperature sensing element may include determining the flow rate of heat energy across at temperature sensing electrode disposed about an outer periphery the first and/or second electrically-conductive plates.

In aspects, the flow rate of heat energy across the temperature sensing element is determined in accordance with a temperature differential between first and second sides of the temperature sensing element and a thermal conductivity of the temperature sensing element.

In aspects, controlling active cooling of tissue based upon the flow rate of heat energy includes selectively applying power to a thermoelectric cooler.

In aspects, both the energy applied to tissue and active cooling of tissue are controlled based upon the flow rate of heat energy.

BRIEF DESCRIPTION OF THE DRAWINGS

Various aspects and features of the present disclosure are described herein with reference to the drawings wherein.

DETAILED DESCRIPTION

Figure 1:
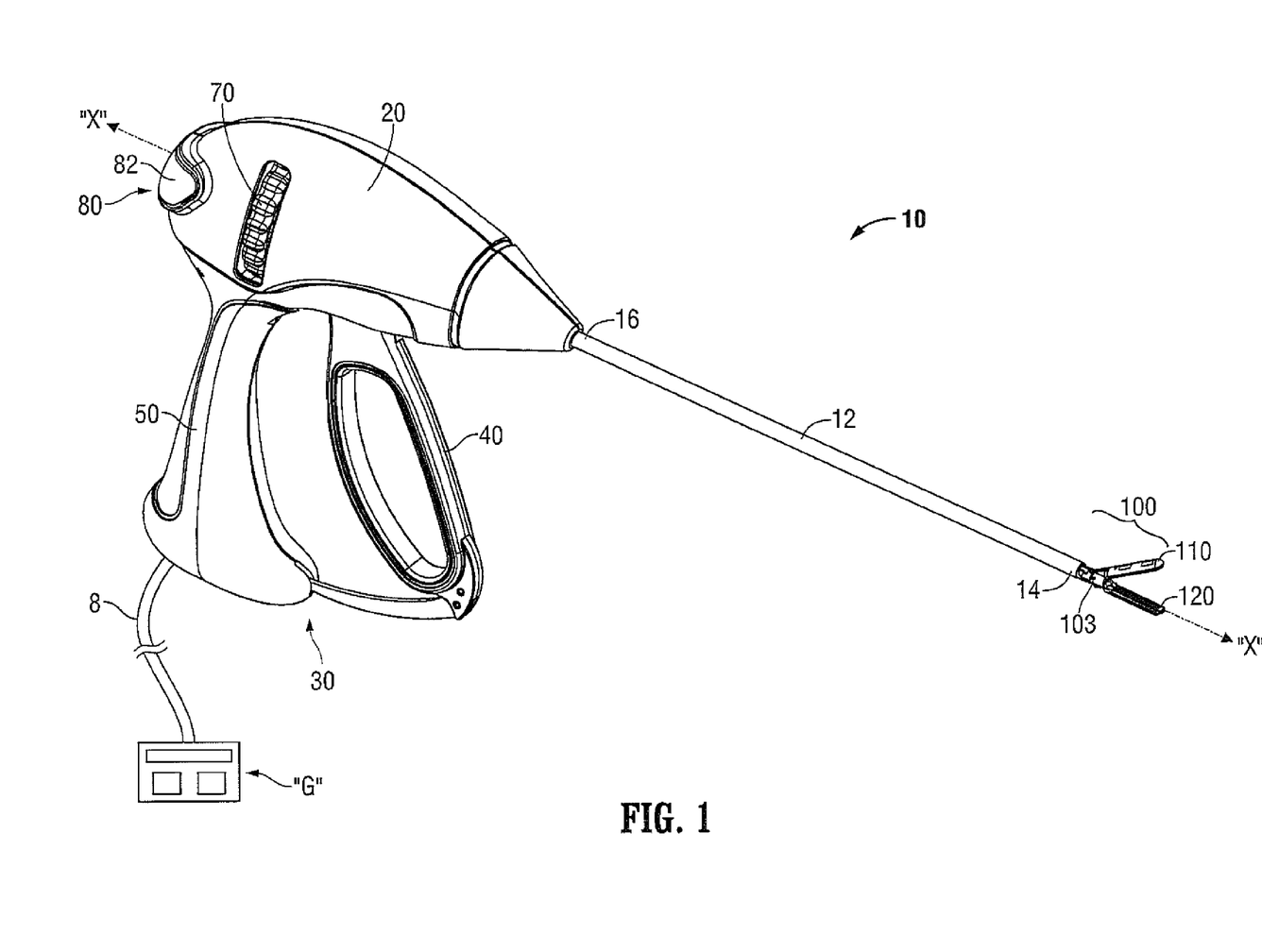
FIG. 1 is a front, side, perspective view of an endoscopic surgical forceps configured for use in accordance with the present disclosure.
Figure 2:
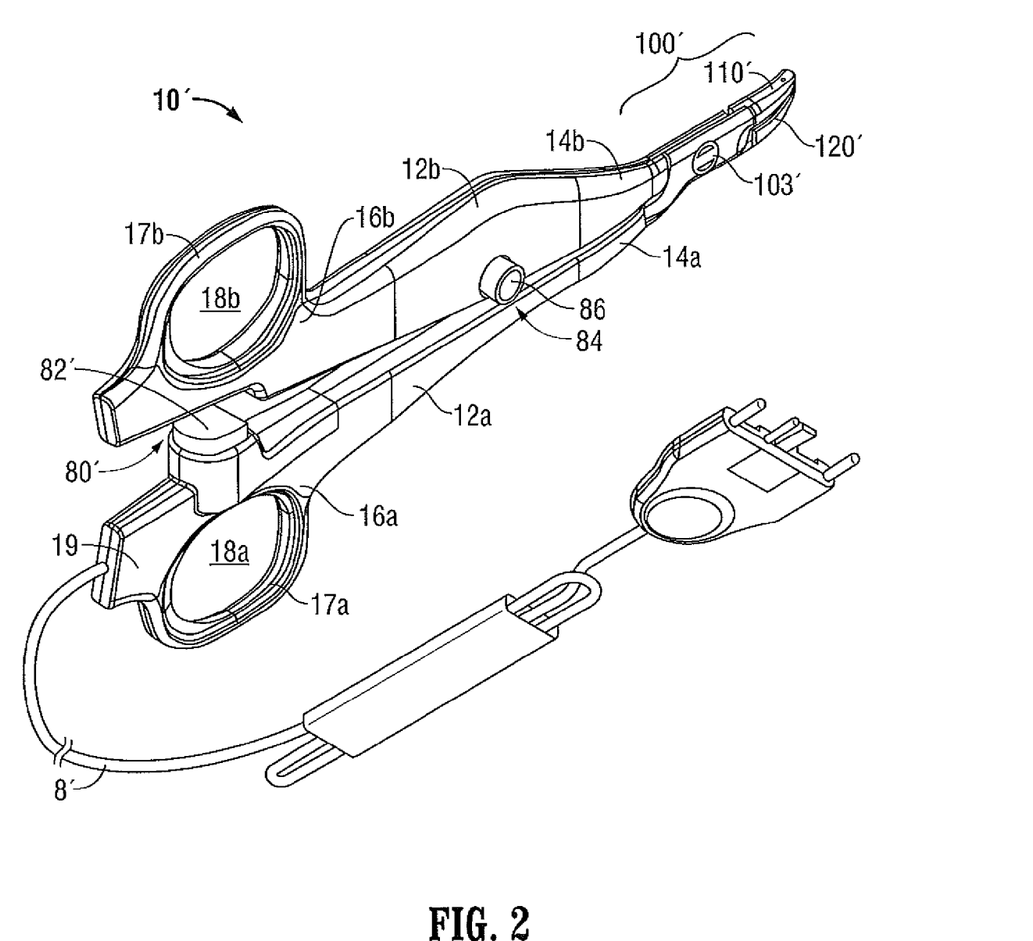
FIG. 2 is a front, side, perspective view of an open surgical forceps configured for use in accordance with the present disclosure.

Turning to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic device, e.g., forceps 10, an open device, e.g., forceps 10', or any other suitable surgical device may be utilized in accordance with the present disclosure. Obviously, different electrical and mechanical connections and considerations apply to each particular type of device, however, the aspects and features of the present disclosure remain generally consistent regardless of the particular device used.

Referring to FIG. 1, an endoscopic forceps 10 is provided defining a longitudinal axis "X" and including a housing 20, a handle assembly 30, a rotating assembly 70, an activation assembly 80, and an end effector assembly 100. Forceps 10 further includes a shaft 12 having a distal end 14 configured to mechanically engage end effector assembly 100 and a proximal end 16 that mechanically engages housing 20. A cable 8 connects forceps 10 to an energy source, e.g., generator "G," although forceps 10 may alternatively be configured as a battery-powered device. Cable 8 includes a wire (or wires) (not shown) extending therethrough that has sufficient length to extend through shaft 12 in order to provide energy to at least one of tissue-contacting plates 114, 124 (FIG. 3A) of jaw members 110, 120, respectively, as well as to energy-based cutting member 130 (FIG. 3A) of jaw member 120. Activation assembly 80 includes a two-mode activation switch 82 provided on housing 20 for selectively supplying energy to jaw members 110, 120 for treating, e.g., sealing, tissue (the first mode), and for energy-based tissue cutting (the second mode).

Handle assembly 30 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of jaw members 110, 120 between a spaced-apart position and an approximated position to grasp tissue between jaw members 110, 120. More specifically, as shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. Rotating assembly 70 is rotatable in either direction about longitudinal axis "X" to rotate end effector 100 about longitudinal axis "X."

Referring to FIG. 2, an open forceps 10' is shown including two elongated shaft members 12a, 12b, each having a proximal end 16a, 16b, and a distal end 14a, 14b, respectively. Forceps 10' is configured for use with an end effector assembly 100' similar to end effector assembly 100 (FIG. 1). More specifically, end effector assembly 100' includes first and second jaw members 110', 120' attached to respective distal ends 14a, 14b of shaft members 12a, 12b. Jaw members 110', 120' are pivotably connected about a pivot 103'. Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of shaft members 12a, 12b relative to one another to, in turn, pivot jaw members 110', 120' from an open position, wherein jaw members 110', 120' are disposed in spaced-apart relation relative to one another, to a closed position, wherein jaw members 110', 120' cooperate to grasp tissue therebetween.

One of the shaft members 12a, 12b of forceps 10', e.g., shaft member 12a, includes a proximal shaft connector 19 configured to connect the forceps 10' to generator "G" (FIG. 1). Proximal shaft connector 19 secures a cable 8' to forceps 10' such that the user may selectively supply energy, e.g., electrosurgical energy, to jaw members 110', 120' for treating, e.g., sealing, tissue and for energy-based tissue cutting. More specifically, a first activation assembly 80' is provided for supplying energy to jaw members 110', 120' to treat tissue upon sufficient approximation of shaft members 12a, 12b, e.g., upon activation of activation button 82' via shaft member 12a. A second activation assembly 84 including a selectively depressible activation button 86 is provided one of the shaft members 12a, 12b, e.g., shaft member 12b, for selectively supplying energy, e.g., electrosurgical energy, to either or both of jaw members 110', 120' for energy-based tissue cutting.

Figure 3A:
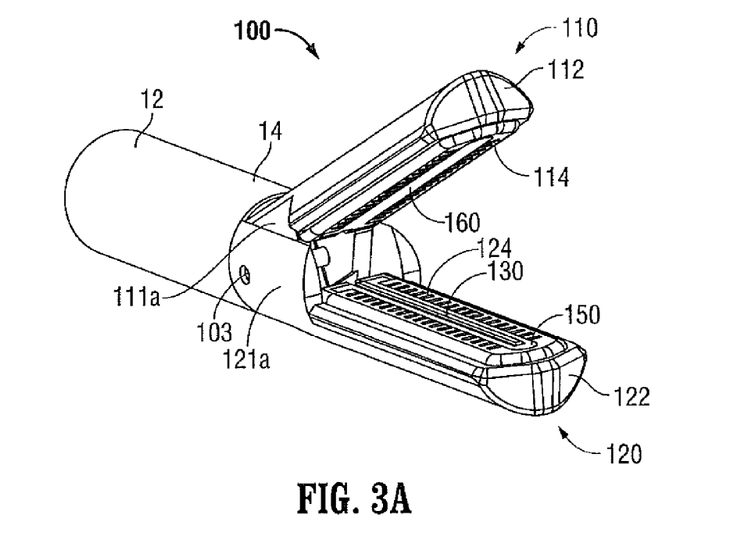
FIG. 3A is a front, side, perspective view of an end effector assembly configured for use with the forceps of FIG. 1 or 2.
Figure 3B:
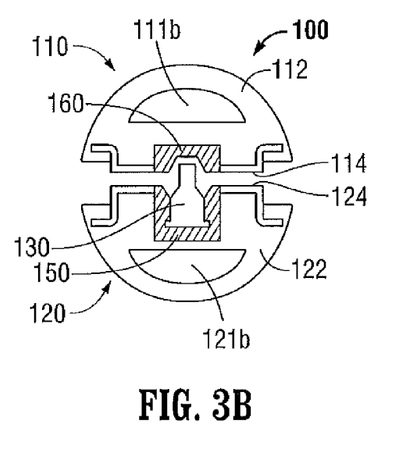
FIG. 3B is a transverse, cross-sectional view of the end effector assembly of FIG. 3A.

With reference to FIGS. 3A and 3B, end effector assembly 100 of forceps 10 (FIG. 1) is shown, although end effector assembly 100' may similarly be used in conjunction with forceps 10' (FIG. 2), or any other suitable surgical device. For purposes of simplicity, end effector assembly 100 is described herein as configured for use with forceps 10 (FIG. 1).

Each jaw member 110, 120 of end effector assembly 100 includes a proximal flange portion 111a, 121a, a distal jaw portion 111b, 121b, an outer insulative jaw housing 112, 122, and a tissue-contacting plate 114, 124, respectively. Proximal flange portions 111a, 121a of jaw members 110, 120 are pivotably coupled to one another about pivot 103 for moving jaw members 110, 120 between the spaced-apart and approximated positions. Distal jaw portions 111b, 121b of jaw members 110, 120 are configured to support jaw housings 112, 122, and tissue-contacting plates 114, 124, respectively, thereon. Further, one of the jaw members 110, 120, e.g., jaw members 120, includes an energy-based cutting member 130 disposed thereon.

Tissue-contacting plates 114, 124 are formed from an electrically conductive material, e.g., for conducting electrical energy therebetween for treating tissue, although tissue-contacting plates 114, 124 may alternatively be configured to conduct any suitable energy through tissue grasped therebetween for energy-based tissue treatment, e.g., tissue sealing. Energy-based cutting member 130 is likewise formed from an electrically conductive material, e.g., for conducting electrical energy between energy-based cutting member 130 and one or both of tissue-contacting plates 114, 124 for electrically cutting tissue, although energy-based cutting member 130 may alternatively be configured to conduct any suitable energy through tissue for electrically cutting tissue.

Tissue-contacting plates 114, 124 are coupled to activation switch 82 (FIG. 1) and generator "G" (FIG. 1) or other suitable source of energy, e.g., via the wires (not shown) extending from cable 8 (FIG. 1) through forceps 10 (FIG. 1), such that energy, e.g., electrosurgical energy, may be selectively supplied to tissue-contacting plate 114 and/or tissue-contacting plate 124 and conducted therebetween and through tissue disposed between jaw members 110, 120 to treat, e.g., seal, tissue in a first mode of operation. Likewise, cutting member 130 is similarly coupled to activation switch 82 (FIG. 1) and generator "G" (FIG. 1) such that energy, e.g., electrosurgical energy, may be selectively supplied to cutting member 130 and conducted through tissue disposed between jaw members 110, 120 to either or both of tissue-contacting plates 114, 124 to cut tissue in a second mode of operation. A first insulating member 150 surrounds cutting member 130 to insulate tissue-contacting plate 124 and cutting member 130 from one another. A second insulating member 160 disposed within a longitudinal slot defined within tissue-contacting plate 114 of jaw member 110 opposes cutting member 130 to insulate cutting member 130 from tissue-contacting plate 114 of jaw member 110 when jaw members 110, 120 are disposed in the approximated position.

Figure 4:
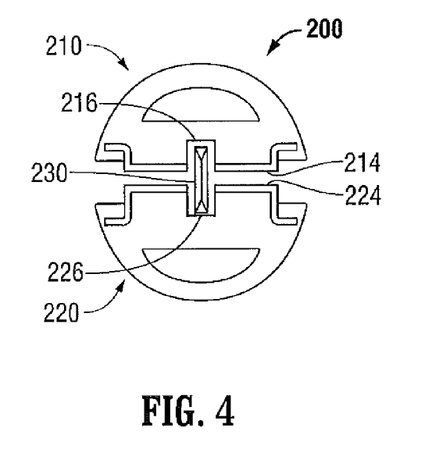
FIG. 4 is a transverse, cross-sectional view of another end effector assembly configured for use with the forceps of FIG. 1 or 2.

Turning to FIG. 4, another embodiment of an end effector assembly configured for use with either forceps 10 (FIG. 1) or forceps 10' (FIG. 2) is shown generally identified by reference numeral 200. End effector assembly 200 is similar to end effector assembly 100 (FIGS. 3A-3B) and, thus, only the differences therebetween will be described in detail below for purposes of brevity.

End effector assembly 200 includes first and second jaw members 210, 220, each including a tissue-contacting plate 214, 224 and a longitudinally-extending slot 216, 226, respectively. A cutting member 230 is configured for longitudinal translation through slots 216, 226 of jaw members 210, 220, e.g., upon activation of a trigger (not shown) operably coupled to cutting member 230, to cut mechanically tissue grasped between jaw members 210, 220. Cutting member 230 may be configured for mechanical cutting, or may be energizable, e.g., via electrical coupling to generator "G" (FIG. 1) via the one or more wires (not shown) of cable 8 (FIG. 1), for electro-mechanically cutting tissue.

Figures 5A, 5B:
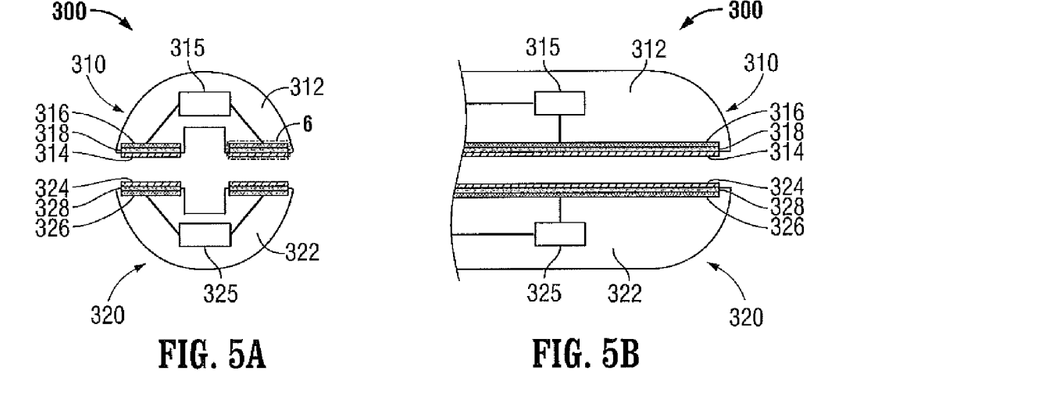
FIG. 5A is a transverse, cross-sectional view of an end effector assembly provided in accordance with the present disclosure incorporating a thermal spread control assembly.
FIG. 5B is a longitudinal, cross-sectional view of the end effector assembly of FIG. 5A.
Figure 6:
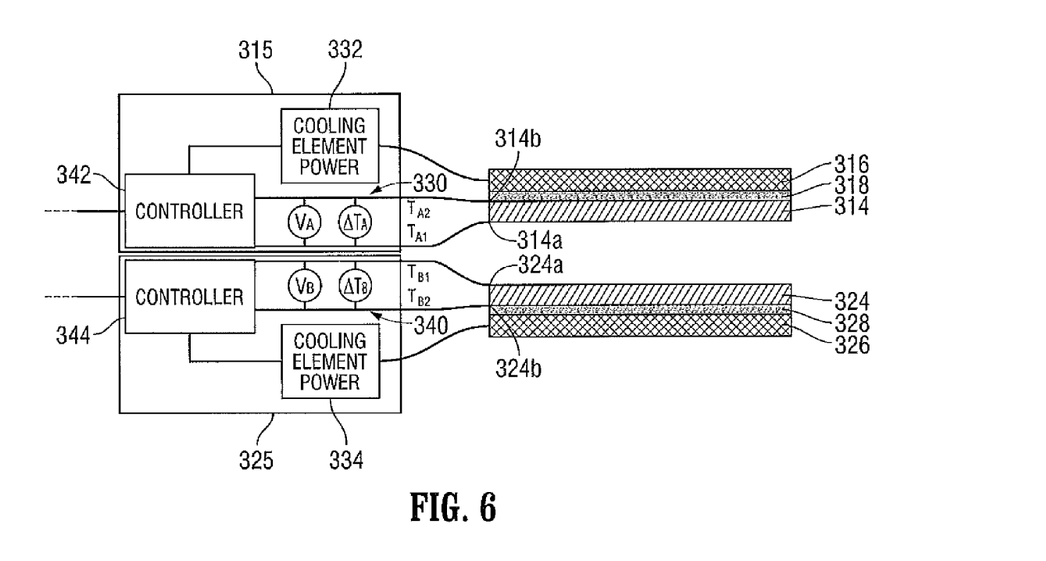
FIG. 6 is an enlarged, schematic illustration of the area of detail indicated as "6" in FIG. 5A.

Turning now to FIGS. 5A-6, one embodiment of an end effector assembly, similar to end effector assemblies 100, 200 (FIGS. 3A-3B and 4, respectively), and configured for use with forceps 10 (FIG. 1), forceps 10' (FIG. 2), or any other suitable surgical instrument, is shown generally designated by reference numeral 300. As will be described in greater detail below, end effector assembly 300 is configured to provide thermal spread control during tissue treatment, e.g., tissue sealing, and, in embodiments where electrical tissue cutting is provided (see FIGS. 3A-3B), to likewise provide thermal spread control during tissue cutting.

End effector assembly 300 includes first and second jaw members 310, 320, each including an outer jaw housing 312, 322 and a tissue-contacting plate 314, 324, respectively, disposed thereon. End effector assembly 300 further includes a thermal spread control assembly 315, 325 embedded within either or both of jaw members 310, 320, although thermal spread control assemblies 315, 325 (or a single thermal spread control assembly) may alternatively be disposed within a remote portion of the surgical instrument, e.g., housing 20 (FIG. 1), or within an external energy source, e.g., generator "G" (FIG. 1). End effector assembly 300 may also include any or all of the features of end effector assemblies 100, 200 (FIGS. 3A-3B and 4, respectively), described above. However, such features will not be described hereinbelow for purposes of brevity.

Continuing with reference to FIGS. 5A-6, jaw members 310, 320 are movable relative to one another from a spaced-apart position to an approximated position for grasping tissue between tissue-contacting plates 314, 324. Tissue-contacting plates 314, 324, similarly as described above, are coupled to generator "G" (FIG. 1) or other suitable source of energy such that energy, e.g., electrosurgical energy, may be selectively supplied to tissue-contacting plate 314 and/or tissue-contacting plate 324 and conducted therebetween and through tissue disposed between jaw members 310, 320 to treat, e.g., seal, tissue.

Tissue-contacting plates 314, 324 of jaw members 310, 320, respectively, each include first and second sides 314a, 324a and 314b, 324b, respectively. First sides 314a, 324a of tissue-contacting plates 314, 324, respectively, are positioned to oppose one another and are configured to grasp tissue therebetween. Second sides 314b, 324b of tissue-contacting plates 314, 324, on the other hand, are positioned adjacent respective outer jaw housings 312, 322, respectively. Tissue-contacting plates 314, 324, in addition to being configured as energizable electrodes for treating tissue, as described above, are also configured as temperature-sensing electrodes, as will be described in greater detail below.

Jaw members 310, 320 each further include a cooling element 316, 326, e.g., a thermoelectric or Peltier cooler, disposed adjacent respective tissue-contacting plates 314, 324. More specifically, cooling elements 316, 326 are positioned adjacent second sides 314b, 324b of tissue-contacting plates 314, 324, respectively, so as to not interfere with the grasping of tissue between first sides 314a, 324a of tissue-contacting plates 314, 324, respectively, and are dimensioned similarly to tissue-contacting plates 314, 324 to substantially extend across the respective second sides 314b, 324b thereof. Cooling elements 316, 326 may be coupled to power sources 332, 334, e.g., batteries, of thermal spread control assemblies 315, 325, respectively, for powering cooling elements 316, 326, although cooling elements 316, 326 may alternatively be coupled to generator "G" (FIG. 6) for this purpose.

A thermally-conductive, electrically-insulative pad 318, 328 is disposed between each of tissue-contacting plates 314, 324 and its respective cooling element 316, 326. As can be appreciated, pads 318, 328 electrically-insulate tissue-contacting plates 314, 324 from cooling elements 316, 326, respectively, but permit thermal conduction therebetween, thus allowing for cooling elements 316, 326 to selectively cool tissue-contacting plates 314, 324, as will be described in greater detail below.

Referring still to FIGS. 5A-6, and to FIG. 6 in particular, tissue-contacting plates 314, 324, in conjunction with cooling elements 316, 326, provide active thermal spread control for minimizing thermal spread to tissue disposed outside of jaw members 310, 320 during tissue treatment (and/or electrical tissue cutting), e.g., during application of energy to tissue grasped between jaw members 310, 320. More specifically, as will be described in greater detail below, thermal spread control assemblies 315, 325 are coupled to both tissue-contacting plates 314, 324 and cooling elements 316, 326 to provide tissue-site feedback-based control of the energy supplied to tissue-contacting plates 314, 324 and/or the power supplied to cooling elements 316, 326 so as to minimize thermal spread outside of the treatment area, e.g., outside of jaw members 310, 320.

Thermal spread control assemblies 315, 325 include sensing circuits 330, 340 coupled to the respective tissue-contacting plates 314, 324 for measuring the temperature differential $\Delta T_A = T_{A1} - T_{A2}$, $\Delta T_B = T_{BS} - T_{B2}$ between the respective first and second sides 314a, 324a and 314b, 324b of tissue-contacting plates 314, 324. Based upon the temperature differentials $\Delta T_A$, $\Delta T_B$, and given a known thermal conductivity, K, for tissue-contacting plates 314, 324, the flow rate of heat energy, Q, through each tissue-contacting plate 314, 324, can be determined in accordance with:

$$Q = \kappa A \frac{\Delta T}{d},$$

where: "κ" is the thermal conductivity, W/m*κ, "Q" is the rate of heat flow, W, "A" is the contact area, "d" is the distance of heat flow, and "ΔT" is the temperature difference.

In addition to measuring the temperature differentials $\Delta T_A$, $\Delta T_B$, monitoring the temperatures $T_{A1}$, $T_{B1}$ at first sides 314a, 324a of tissue-contacting plates 314, 324, respectively, provides a measure of the tissue treatment temperature ($T_{tt}$) as a function of the applied energy. Controlling the tissue treatment temperature ($T_{tt}$), in conjunction with thermal spread control with applied tissue treatment energy, simultaneously provides controlled tissue treatment efficacy. Tissue temperature control provides another means of thermal spread control through the monitored tissue temperatures $T_{A1}$, $T_{B1}$ at first sides 314a, 324a of tissue-contacting plates 314, 324, respectively. Note that the tissue treatment temperature as a function of time, $T_{tt}/dt = T_{A1}/dt$ or $T_{B1}/dt$, when monitored, can be utilized to control the tissue treatment temperature rate of change. Monitoring the tissue temperature difference $T_{A1} - T_{B1}$ between the first sides 314a, 324a of tissue-contacting plates 314, 324, provides a uniformity measure of thermal tissue heating and/or a tissue temperature gradient with applied treatment energy.

Sensing circuits 330, 340 are further configured to measure the voltages $V_A$, $V_B$ across tissue-contacting plates 314, 324. Based upon a known electrode resistivity (ρ) for tissue contacting plates 314, 324, as expressed by electrode resistance R(Ω), a measure of the tissue-delivered RF current (I) passing through the treatment tissue as monitored by $V_A$ and $V_B$ can be determined in accordance with:

$$R(\Omega) = \frac{\rho l}{A},$$

where "R" is the electrode resistance, "ρ" is the electrode resistivity, "l" is the electrode length, and "A" is the electrode area. Thus, the tissue-delivered RF current can be measured at either tissue-contacting plates 314, 324 according to:

$$RFCurrent(I) = \frac{V_A}{[R(\Omega), 314]} = \frac{V_B}{[R(\Omega), 324]}.$$

Accordingly, and as will be described in greater detail below, using the flow rate of heat, Q, through tissue-contacting plates 314, 324, thermal spread control assemblies 315, 325 can control the energy (a function of $V_A$, $V_B$, $\Delta T_A$, $\Delta T_B$, $T_{A1}$, and $T_{B1}$) by monitoring tissue-contacting plates 314, 324 and/or the power supplied to cooling elements 316, 326 (via power sources 332, 334) for actively cooling tissue-contacting plates 314, 324, to minimize thermal spread.

Continuing with particular reference to FIG. 6, as mentioned above, sensing circuits 330, 340 of thermal spread control assemblies 315, 325, respectively, are configured to measure the temperature differentials $\Delta T_A$, $\Delta T_B$ between the first and second sides 314a, 324a and 314b, 324b of tissue-contacting plates 314, 324 and the voltages $V_A$, $V_B$ across tissue-contacting plates 314, 324, respectively. This sensed data is transmitted to controllers 342, 344 of thermal spread control assemblies 315, 325, which calculate the flow rate of heat energy, Q, through respective tissue-contacting plates 314, 324, and control the energy, e.g., voltages $V_A$, $V_B$, supplied to tissue-contacting plates 314, 324, as well as the power supplied to cooling elements 316, 326 in accordance therewith.

It has been found that an increased flow rate of heat energy, Q, through tissue-contacting plates 314, 324 is an indication of increased thermal spread, or an increased potential of thermal spread. Accordingly, controllers 342, 344 may be configured such that, when the flow rate of heat energy, Q, across either or both tissue-contacting plates 314, 324 exceeds a pre-determined threshold, controllers 342, 344 direct power sources 332, 334 to increase the supply of power to cooling elements 316, 326 and/or reduce the energy supplied to tissue-contacting plates 314, 324, e.g., reduce voltages $V_A$, $V_B$ or the gradient therebetween. Increasing the power supplied to cooling elements 316, 326 enhances the cooling effect of cooling elements 316, 326, thereby increasing the cooling of tissue-contacting plates 314, 324 and, thus, the cooling of tissue adjacent thereto. Reducing the supply of energy to tissue-contacting plates 314, 324 reduces the amount of energy conducted through tissue grasped therebetween and, thus, reduces the heating of tissue. As can be appreciated, each of these has the effect of reducing thermal spread.

As detailed above, controllers 342, 344, based on the sensed data received from sensing circuits 330, 340, control the supply of power to cooling elements 316, 326 and/or the energy supplied to tissue-contacting plates 314, 324, in order to control thermal spread. More specifically, controllers 342, 344 may be configured to maintain the flow rate of heat energy, Q, below a pre-determined threshold, or within a pre-determined range via the tissue-site feedback-based control loop described above. The particular threshold or range may be set in controllers 342, 344, adjustable via a user (using generator "G" (FIG. 1), or may be automatically determined by controllers 342, 344 based upon sensed conditions, e.g., tissue impedance, distance between tissue-contacting plates 314, 324, grasping pressure applied to tissue between tissue-contacting plates 314, 324, etc.

Figure 7A:
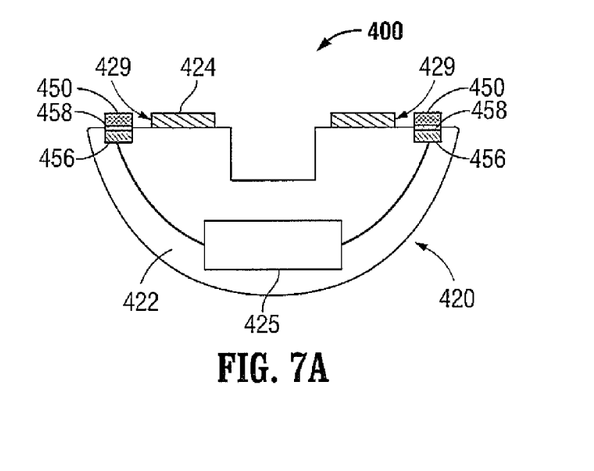
FIG. 7A is a transverse, cross-sectional view of a jaw member of an end effector assembly provided in accordance with the present disclosure incorporating another thermal spread control assembly
Figure 7B:
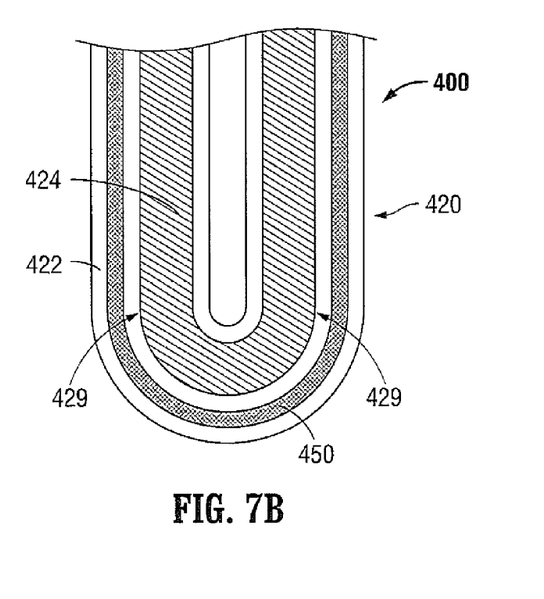
FIG. 7B is a top view of the jaw member of FIG. 7A.

Turning now to FIGS. 7A-7B, another embodiment of an end effector assembly (with one of the jaw members removed) provided in accordance with the present disclosure and configured to provide thermal spread control during application of energy to tissue is shown generally designated by reference numeral 400. End effector assembly 400 is similar to end effector assembly 300 (FIGS. 5A-6) and, thus, only the differences therebetween will be described in detail below for purposes of brevity. Further, the jaw members of end effector assembly 400 are similar to one another and, thus, only jaw member 420 is shown in the drawings and described below.

With continued reference to FIGS. 7A-7B, jaw member 420 includes an outer jaw housing 422 and a tissue-contacting plate 424, respectively, disposed thereon. A thermal spread control assembly 425 is embedded within jaw member 420, although thermal spread control assembly 425 may alternatively be remotely disposed. Tissue-contacting plate 424, is coupled to generator "G" (FIG. 1) or other suitable source of energy such for conducting energy through tissue to treat, e.g., seal, tissue. Tissue-contacting plate 424 defines an outer periphery 429.

Jaw member 420 further include a thermal sensing electrode 450 disposed on jaw housing 422. Thermal sensing 450 electrode is spaced-apart from and disposed about the outer periphery 429 of tissue-contacting plate 424. Thermal sensing electrode 450 is generally co-planar with tissue-contacting plate 424. A cooling element 456, e.g., a thermoelectric or Peltier cooler, is disposed adjacent thermal sensing electrode 450 on the jaw member side thereof, similarly as described above with respect to tissue-contacting plates 314, 324 and cooling elements 316, 326, respectively (see FIGS. 5A-6). Further, a thermally-conductive, electrically-insulative pad 458 is disposed between thermal sensing electrode 450 and cooling element 456 to electrically-insulate thermal sensing electrode 450 and cooling element 456 from one another while permitting thermal conduction therebetween, thus allowing for cooling element 456 to selectively cool thermal sensing electrode 450, thereby controlling thermal spread beyond end effector assembly 400.

Referring still to FIGS. 7A-7B, thermal sensing electrode 450 and cooling element 456 provide active thermal spread control for minimizing thermal spread to tissue disposed outside of end effector assembly 400 during tissue treatment (and/or electrical tissue cutting). More specifically, a thermal spread control assembly 425 is coupled to both thermal sensing electrode 450 and cooling element 456 to provide tissue-site feedback-based control of the energy supplied to tissue-contacting plate 424 and/or the power supplied to cooling element 456 so as to minimize thermal spread outside of the treatment area, e.g., outside of end effector assembly. Thermal spread assembly 425 may be configured for use with thermal sensing electrode 450 and cooling element 456 similarly as described above with respect to thermal spread assemblies 315, 325 use with tissue-contacting surfaces 314, 324 and cooling elements 316, 326, (FIGS. 5A-6).

Figure 8:
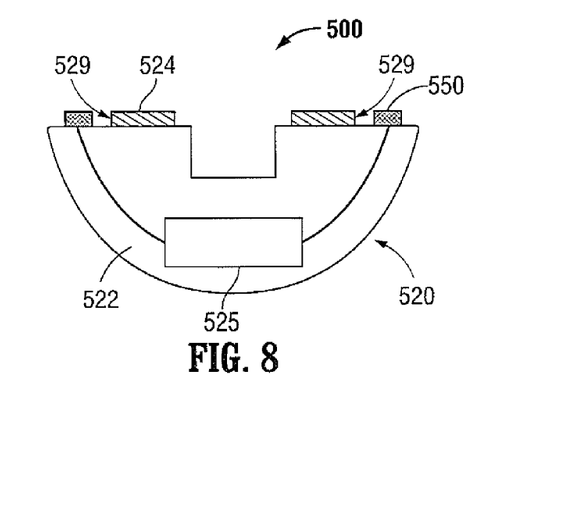
FIG. 8 is a transverse, cross-sectional view of a jaw member of an end effector assembly provided in accordance with the present disclosure incorporating another thermal spread control assembly.

With reference to FIG. 8, another embodiment of an end effector assembly (with one of the jaw members removed) provided in accordance with the present disclosure and configured to provide thermal spread control during application of energy to tissue is shown generally designated by reference numeral 500. End effector assembly 500 is similar to end effector assembly 400 (FIGS. 7A-7B) and, thus, only the differences therebetween will be described in detail below for purposes of brevity. Further, the jaw members of end effector assembly 500 are similar to one another and, thus, only jaw member 520 is shown in the drawings and described below.

Jaw member 520 of end effector assembly 500 is similar to jaw member 420 (FIGS. 7A-7B), except that, rather than providing active cooling to control thermal spread, e.g., using a thermoelectric or Peltier cooler, jaw member 520 provides for passive cooling. Jaw member 520 includes an outer jaw housing 522 and a tissue-contacting plate 524, respectively, disposed thereon. Tissue-contacting plate 524, is coupled to generator "G" (FIG. 1) or other suitable source of energy such for conducting energy through tissue to treat, e.g., seal, tissue. Tissue-contacting plate 524 defines an outer periphery 529.

Jaw member 520 further includes a thermal sensing electrode 550 disposed on jaw housing 522. Thermal sensing electrode 550 is spaced-apart from and disposed about the outer periphery 529 of tissue-contacting plate 524. Thermal sensing electrode 550 is configured to passively absorb heat from tissue adjacent thereto to reduce thermal spread beyond end effector assembly 500. Thermal sensing electrode 550 is also coupled to a thermal spread control assembly 525 that, similarly as described above with respect to previous embodiments, provides tissue-site feedback-based control of the energy supplied to tissue-contacting plate 524 based upon the flow rate of heat energy, Q, across thermal sensing electrode 550, so as to minimize thermal spread outside of the treatment area, e.g., outside of end effector assembly.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in, scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   at least one electrically-conductive plate adapted to connect to a source of energy for supplying energy to tissue to treat tissue;
   a temperature sensing element; and
   a thermal spread control assembly coupled to the temperature sensing element, the thermal spread control assembly configured to determine a flow rate of heat energy across the temperature sensing element and to at least one of: control the energy applied to the at least one electrically-conductive plate and control active cooling of the temperature sensing element, in accordance with the determined flow rate of heat energy.

2. The surgical instrument according to claim 1, wherein the temperature sensing element is incorporated into the electrically-conductive plate.

3. The surgical instrument according to claim 1, wherein the temperature sensing element is disposed about an outer periphery of the electrically-conductive plate.

4. The surgical instrument according to claim 1, further comprising a thermoelectric cooler coupled to the temperature sensing element for actively cooling the temperature sensing element.

5. The surgical instrument according to claim 4, wherein the thermal spread control assembly controls power supplied to the thermoelectric cooler to vary an amount of cooling provided by the thermal spread control assembly.

6. The surgical instrument according to claim 4, further comprising a thermally-conductive, electrically insulative material disposed between the thermoelectric cooler and the temperature sensing element.

7. The surgical instrument according to claim 1, wherein the thermal spread control assembly is configured to measure a temperature at each of a first side and a second side of the temperature sensing element to determine a temperature differential therebetween.

8. The surgical instrument according to claim 7, wherein the thermal spread control assembly is configured to determine the flow rate of heat energy across the temperature sensing element in accordance with the temperature differential and a thermal conductivity of the temperature sensing element.

9. The surgical instrument according to claim 1, wherein the at least one electrically-conductive plate and the temperature sensing element are disposed within an end effector assembly of the surgical instrument.

10. The surgical instrument according to claim 9, wherein the thermal spread control assembly is disposed within the end effector assembly.

11. The surgical instrument according to claim 9, wherein the thermal spread control assembly is remotely positioned relative to the end effector assembly.

12. The surgical instrument according to claim 1, wherein the thermal spread control assembly performs control in accordance with the determined flow rate of heat energy to maintain the flow rate of heat energy within a predetermined range.

13. The surgical instrument according to claim 1, wherein the thermal spread control assembly performs control in accordance with the determined flow rate of heat energy to maintain the flow rate of heat energy below a predetermined threshold.

14. A method of treating tissue, comprising:
applying energy to tissue;
determining a flow rate of heat energy across a temperature sensing element; and
controlling at least one of the energy applied to tissue and active cooling of tissue based upon the flow rate of heat energy.

15. The method according to claim 14, wherein the step of applying energy to tissue includes grasping tissue between first and second electrically-conductive plates and conducting energy therebetween.

16. The method according to claim 15, wherein the step of determining the flow rate of heat energy across the temperature sensing element includes determining the flow rate of heat energy across at least one of first and second electrically-conductive plates.

17. The method according to claim 15, wherein the step of determining the flow rate of heat energy across the temperature sensing element includes determining the flow rate of heat energy across at temperature sensing electrode disposed about an outer periphery of least one of first and second electrically-conductive plates.

18. The method according to claim 14, wherein the flow rate of heat energy across the temperature sensing element is determined in accordance with a temperature differential between first and second sides of the temperature sensing element and a thermal conductivity of the temperature sensing element.

19. The method according to claim 14, wherein controlling active cooling of tissue based upon the flow rate of heat energy includes selectively applying power to a thermoelectric cooler.

20. The method according to claim 14, further comprising the step of controlling both the energy applied to tissue and active cooling of tissue based upon the flow rate of heat energy.

* * * * *